United States Patent
Ollmar et al.

(10) Patent No.: US 9,022,932 B2
(45) Date of Patent: May 5, 2015

(54) METHOD AND APPARATUS FOR MEASURING GLUCOSE IN BODY FLUIDS USING SUB-DERMAL BODY TISSUE IMPEDANCE MEASUREMENTS

(75) Inventors: Stig Ollmar, Huddinge (SE); Peter Aberg, Enskede (SE); Ulrik Birgersson, Stockholm (SE); Fredrik Neiderud, Sollentuna (SE)

(73) Assignee: Dermal Devices, Inc., London (CA)

( * ) Notice: Subject to any disclaimer, the term of this patent is extended or adjusted under 35 U.S.C. 154(b) by 652 days.

(21) Appl. No.: 10/588,551

(22) PCT Filed: Feb. 4, 2005

(86) PCT No.: PCT/CA2005/000148
§ 371 (c)(1),
(2), (4) Date: Aug. 7, 2006

(87) PCT Pub. No.: WO2005/074796
PCT Pub. Date: Aug. 18, 2005

(65) Prior Publication Data
US 2007/0161881 A1    Jul. 12, 2007

Related U.S. Application Data

(60) Provisional application No. 60/541,748, filed on Feb. 5, 2004.

(51) Int. Cl.
*A61B 5/05* (2006.01)
*A61B 5/145* (2006.01)
(Continued)

(52) U.S. Cl.
CPC ........... *A61B 5/14532* (2013.01); *A61B 5/0402* (2013.01); *A61B 5/053* (2013.01)

(58) Field of Classification Search
USPC .................................. 600/345–347, 365, 357
See application file for complete search history.

(56) References Cited

U.S. PATENT DOCUMENTS

| | | |
|---|---|---|
| 5,036,861 A | 8/1991 | Sembrowich et al. |
| 5,115,133 A | 5/1992 | Knudson |

(Continued)

FOREIGN PATENT DOCUMENTS

| | | |
|---|---|---|
| EP | 1 437 091 | 7/2004 |
| WO | WO-94/20602 | 9/1994 |

(Continued)

OTHER PUBLICATIONS

Nicander, Ingrid, "Electrical impedance related to experimentally induced changes of human skin and oral mucosa" 1998, pp. 1-86, Kongl Carolnska Medico Chirurgiska Institutet, Stockholm.

(Continued)

*Primary Examiner* — Michael D'Angelo
(74) *Attorney, Agent, or Firm* — B. Aaron Schulman, Esq.; Stites & Harbison, PLLC.

(57) ABSTRACT

A method and an apparatus for measuring glucose level in the body fluid of a subject, typically blood glucose level, by measuring impedance of a body tissue, with two pairs of electrodes, two electrodes for injecting current into a body tissue and two electrodes for detecting the ensuing voltage of the body tissue. The body tissue is typically a sub-dermal or sub-cutaneous tissue. The measured impedance of the body tissue is used to correlate with directly determined glucose levels to determine the glucose level from the measured impedance. It is thus possible to determine body fluid glucose levels in a reliable and reproducible manner.

13 Claims, 11 Drawing Sheets

(51) Int. Cl.
*A61B 5/053* (2006.01)
*A61B 5/0402* (2006.01)

(56) References Cited

U.S. PATENT DOCUMENTS

| | | | |
|---|---|---|---|
| 5,146,091 A | | 9/1992 | Knudson |
| 5,179,951 A | | 1/1993 | Knudson |
| 5,222,496 A | | 6/1993 | Clarke et al. |
| 5,353,802 A | | 10/1994 | Ollmar |
| 5,433,197 A | | 7/1995 | Stark |
| 5,680,858 A | | 10/1997 | Hansen et al. |
| 5,792,668 A | | 8/1998 | Fuller et al. |
| 5,890,489 A | | 4/1999 | Elden |
| 6,322,963 B1 * | | 11/2001 | Bauer ............................ 435/4 |
| 6,424,847 B1 * | | 7/2002 | Mastrototaro et al. ........ 600/316 |
| 6,514,718 B2 | | 2/2003 | Heller et al. |
| 6,517,482 B1 * | | 2/2003 | Elden et al. ................... 600/309 |
| 7,315,767 B2 * | | 1/2008 | Caduff et al. .................. 700/266 |
| 2002/0049389 A1 * | | 4/2002 | Abreu ............................ 600/558 |
| 2003/0130616 A1 * | | 7/2003 | Steil et al. ....................... 604/66 |
| 2003/0216663 A1 * | | 11/2003 | Jersey-Willuhn et al. .... 600/547 |
| 2003/0220581 A1 * | | 11/2003 | Ollmar et al. ................. 600/547 |
| 2004/0182719 A1 * | | 9/2004 | Purvis et al. ................... 205/414 |
| 2005/0192488 A1 * | | 9/2005 | Bryenton et al. ............. 600/301 |

FOREIGN PATENT DOCUMENTS

| | | |
|---|---|---|
| WO | WO-98/04190 | 2/1998 |
| WO | WO-99/39627 | 8/1999 |
| WO | WO-01/26538 | 4/2001 |

OTHER PUBLICATIONS

Aberg et al, "Minimally invasive electrical impedance spectroscopy of skin exemplified by skin cancer assessments" 2003, pp. 3211-3214, Proceed. of 2th Annual Int'l Conf. of the IEEE EMBS, Cancun, Mexico.

Ollmar et al, "The modeling of cellular media in electrical impedance tomography" 1995, pp. 745-750, vol. 16, No. 6, Innovation Et Technolgie En Biologie Et Medecine.

Min et al, "Electrical Impedance and Cardiac Monitoring—Technology, Potential and Applications" 2003, pp. 53-56 vol. 5, No. 1, International Journal of Bioelectromagnetism.

Beetner et al, "Differentiation Among Basal Cell Carcinoma, Benign Lesions, and Normal Skin Using Electric Impedance", 2002, pp. 1-7.

Parkes et al., "A New Consensus Error Grid to Evaluate the Clinical Significance of Inaccuracies in the Measurement of Blood Glucose", pp. 1143-1148, Diabetes Care, vol. 23, No. 8, Aug. 2000.

Clarke et al., "Evaluating Clinical Accuracy of Systems for Self-Monitoring of Blood Glucose", pp. 622-628, Diabetes Care, vol. 10, No. 5, Sep.-Oct. 1987.

Koschinsky et al., "Clarification of Error-Grid Analysis", pp. 235-238, Diabetes Care, vol. 12, No. 3, Mar. 1989.

Koschinsky et al., "Sensors for Glucose Monitoring: Technical and Clinical Aspects", Diabetes/Metabolism Research and Reviews, Rev 2001; pp. 113-123.

Nicander et al., "Electrical impedance measured to five skin depths in mild irritant dermatitis induced by sodium lauryl sulphate", pp. 718-724, 1995 British Journal of Dermatology.

Nicander et al., "Correlation of impedance response patterns to histological findings in irritant skin reactions induced by various surfactants", pp. 221-228, 1996 British Journal of Dermatology.

Ollmar et al., "Information in full and reduced data sets of electrical impedance spectra from various skin conditions, compared using a holographic neural network", pp. 415-419, Medical & Biological Engineering & Computing, Jul. 1997.

Nicander et al., "Baseline electrical impedance measurement at various skin sites—related to age and sex", pp. 252-258, 1997 Skin Research and Technology.

Nicander et al., "Electrical impedance and other physical parameters as related to lipid content of human stratum corneum", pp. 1-9, 1998 Skin Research and Technology.

Nicander et al., "Electrical impedance measurements at six different locations of macroscopically normal human oral mucosa", pp. 88-93, 1997 Acta Odontol Scand.

Nicander et al., "Electrical impedance. A method to evaluate subtle changes of the human oral mucosa", Eur J Oral Sci 1997, pp. 576-582.

* cited by examiner

METHOD AND APPARATUS FOR MEASURING GLUCOSE IN BODY FLUIDS USING SUB-DERMAL BODY TISSUE IMPEDANCE MEASUREMENTS

The application claims priority from U.S. Provisional Application No. 60/541,748, filed on Feb. 5, 2004, the entire contents of which are incorporated herein by reference.

FIELD OF INVENTION

The present invention relates to a method and apparatus for determination of glucose level in the body fluid of a subject, typically blood glucose level, by measurement of impedance of a sub-dermal or subcutaneous body tissue.

BACKGROUND OF THE INVENTION

At the present time, patients with diabetes rely on self-monitoring of blood glucose, using an invasive blood glucose meter several times every day. This method typically involves drawing a small sample of blood, which is then tested directly for glucose level. There are numerous drawbacks to this method. The patient must draw samples of blood every day, several times a day at regular intervals. There is some discomfort associated with drawing blood samples repeatedly. Also, there is a margin for error. For example, patients may forget to take blood samples when required. It would be of great economical as well as medical interest to develop a new device for self monitoring of blood glucose that facilitates continuous monitoring of blood glucose level, that is reliable and accurate, but does not negatively impact a patient's quality of life. Health costs would be lowered and the quality of life for diabetes patients would be greatly improved.

There have been attempts at developing non-invasive glucose measurement techniques that are able to monitor blood glucose concentration. Non-invasive measurement systems could minimize the discomfort to patients and also provide more accurate, risk-free measurement of glucose and the required dosage of insulin. By non-invasive techniques, it will be understood that the surface of the skin is not broken and/or samples of body tissues, including bodily fluids such as blood, from patients is not required Some of these methods involve measurement of impedance of certain types of electromagnetic radiation with or through body tissues. This is also known as bioimpedance. Impedance measurements have been used previously to evaluate different types of body conditions. As the total impedance of body tissue depends on a variety of factors, including cellular structure and the composition of both extra and intra cellular fluid, it can be a good diagnostic tool in health care. Body tissue impedance has used in a number of other applications, including estimation of skin irritation from different chemicals (Nicander, I. (1998) "Electrical impedance related to experimentally induced changes of human skin and oral mucosa" PhD thesis, Karolinska Institutet), cardiac monitoring function (Min, M. et al. "Electrical Impedance and Cardiac Monitoring-Technology, Potential and Applications." *International Journal of Bioelectromagnetism*, v. 5: 53-56, 2003), and skin cancer detection (Beetner D. G., et al. (2003): "Differentiation among basal cell carcinoma, benign lesions, and normal skin using electric impedance", *IEEE T Bio-Med Eng*, 50(8), pp 1020-1025; Åberg P. et al. (2003) "Minimally invasive electrical impedance spectroscopy of skin exemplified by skin cancer assessments", *Proc IEEE EMBS*, Cancun (MX), 17-21 Sep. 2003, pp 3211-3214, ISBN 07803-7790-7).

Non-invasive methods for determining blood glucose level, involving measurement of skin tissue impedance have been described. For example, U.S. Pat. No. 5,036,861 (issued to Sembrowich et al. on Aug. 6, 1991) describes a wrist-mountable device having an electrode which measures glucose present in sweat at the skin surface. WO 01/26538 (to Süsstrunk, et al, published Oct. 13, 2000) describes another wrist-mountable device for measurement of blood glucose. U.S. Pat. No. 5,222,496 (issued to Clarke et al. on Jun. 29, 1993) describes an infrared glucose sensor mountable, for instance, on a wrist or finger. U.S. Pat. No. 5,433,197 (issued to Stark on Jul. 18, 1995) describes determination of blood glucose through illuminating a patient's eye with near-infrared radiation. U.S. Pat. Nos. 5,115,133, 5,146,091 and 5,197,951 (issued to Knudson on May 19, 1992, Sep. 8, 1992 and Jan. 19, 1993, respectively) describe measuring blood glucose within blood vessels of a tympanic membrane in a human ear through light absorption measurements. WO 9504496 (to Fuller, published Feb. 16, 1995, describes the use of radio frequency spectroscopy to determine concentrations of blood analytes, including glucose. WO98/04190 (to Elden et al., published Feb. 5, 1998) and WO99/39627 (to Elden et al., published Aug. 12, 1999) describe the use of measuring skin tissue impedance to determine glucose concentration in a body fluid. EP Application No. 1 437 091, to Ollmar et al., published on Jul. 14, 2004 describes a minimally invasive method and apparatus for measuring skin impedance and correlation with blood glucose level, by way of an electrode with micromachined spikes which penetrate the skin surface. Finally, U.S. Pat. No. 5,353,802 (issued to Ollmar on Oct. 11, 1994) describes a probe with a plurality of electrodes for detection and characterization of surface phenomena in a body tissue, by surface measurement of the impedance of the tissue. The specifications of the references cited above are incorporated herein by reference.

There may be difficulties associated with the correlation of skin impedance to glucose levels or concentrations in body fluids. For example, the accuracy and reproducibility of skin impedance measurements can be affected by several factors, including the condition of the skin, which may vary between individuals. Such conditions can include, for example, the thickness of the skin, the location on the body where the impedance measurement is taken, the presence of dirt and/or oils on the surface and/or the presence of inflammation or a disease state affecting the skin. The accuracy and reproducibility of skin impedance measurements is also affected by the nature of skin tissue These difficulties may not be overcome with some prior art devices or methods.

Accordingly, there is a need for a more accurate and reproducible method to allow monitoring of body fluid glucose levels, such as blood glucose levels.

SUMMARY OF THE INVENTION

It is an object of this invention to overcome the difficulties associated with measuring glucose levels or concentrations within a bodily fluid, such as blood via skin impedance. It is another object of the present invention to provide a method and apparatus for measuring or obtaining glucose levels in a body fluid, typically blood. It is a further object of this invention to utilize measurements of sub-dermal or subcutaneous body tissue impedance to determine glucose levels in a body fluid in an accurate and reproducible manner.

In accordance with a broad aspect of the present invention, there is provided a method for monitoring glucose in a body fluid of a subject, comprising measuring impedance of a sub-dermal or subcutaneous body tissue between two injection electrodes for injecting electrical current into said subdermal body tissue and two sensing electrodes for detecting the ensuing voltage of said sub-dermal or subcutaneous body tissue, wherein said injection electrodes and said sensing electrodes are in electrically conductive contact with the a body tissue impedance is measured at a plurality of frequencies in a range of 1 Hz to 10 MHz; and determining the amount of glucose in the body fluid based upon the measured impedance. The current injected into the sub-dermal tissue is forced through regardless of electrode and body tissue impedance at all frequencies in the above-noted range.

In a further embodiment of the invention, the method comprises a first injection electrode and a first sensing electrode which are placed in conductive contact with a body tissue or at a first position on the subject and a second injection electrode and a second sensing electrode are placed in conductive contact with a body tissue at a second position on the subject, and impedance of the sub-dermal body tissue is measured between the first and second positions. The injection electrodes can be in electrically conductive contact with, for example, the skin surface of the subject and the sensing electrodes can be in electrically conductive contact with a sub-dermal or subcutaneous body tissue of the subject. In yet another embodiment, the injection electrodes and sensing electrodes can be implanted within the sub-dermal or subcutaneous body tissue from which the impedance is to be measured. The sub-dermal or subcutaneous body tissue can be muscle, adipose (e.g. fat), blood vessels or blood. The body fluid in which glucose level is to be determined can be blood. It will be understood that the terms "sub-dermal" or "subcutaneous" refer to tissues below the skin or dermis, and can include all tissues except for the skin dermis.

In a further aspect of the invention, the method of determining the amount of glucose includes comparing the measured impedance of sub-dermal or subcutaneous body tissue with a predetermined relationship between impedance of the sub-dermal body tissue and blood glucose level.

In another aspect of the invention, there is provided an apparatus for monitoring glucose in a body fluid of a subject comprising two injection electrodes for injecting electrical current into said sub-dermal or subcutaneous body tissue, two sensing electrodes for detecting the voltage of the sub-dermal or subcutaneous body tissue, said injection electrodes and sensing electrodes being in electrically conductive contact with a body tissue. There is provided a source of electrical current, an amperometer, and a voltmeter for measuring the impedance of the sub-dermal body tissue between said injection electrodes and said sensing electrodes, wherein said electrical current is provided at a plurality of frequencies in a range of 1 Hz to 10 MHz, and wherein the amperometer and source of electric current are in operative connection with the injection electrodes and the voltmeter is in operative connection with the sensing electrodes, and a microprocessor operatively connected to the means for measuring impedance for determining the amount of glucose in the body fluid based upon the impedance measurement.

In a further embodiment of the apparatus of the invention, the microprocessor is operatively connected to an insulin pump and includes means to adjust the amount of insulin flow via the pump to the subject based on the determined blood glucose level. In yet a further embodiment, the apparatus comprises means for calibrating the apparatus against a directly measured glucose level of said subject. The microprocessor can be programmed to determine the glucose level of a subject based on a principal component analysis and a partial least squares regression analysis. There can also be an indicator operatively connected to the microprocessor for indication of the determined amount of glucose. The apparatus can be implanted in the sub-dermal body tissue for which the impedance is to be measured.

Other and further advantages and features of the invention will be apparent to those skilled in the art form the following detailed description of an embodiment thereof, taken in conjunction with the accompanying drawings.

BRIEF DESCRIPTION OF THE DRAWINGS

Various objects, features and attendant advantages of the present invention will become more fully appreciated and better understood when considered in conjunction with the accompanying drawings, in which like reference characters designate the same or similar parts throughout the several views.

DETAILED DESCRIPTION OF THE PREFERRED EMBODIMENTS

Figure 1:
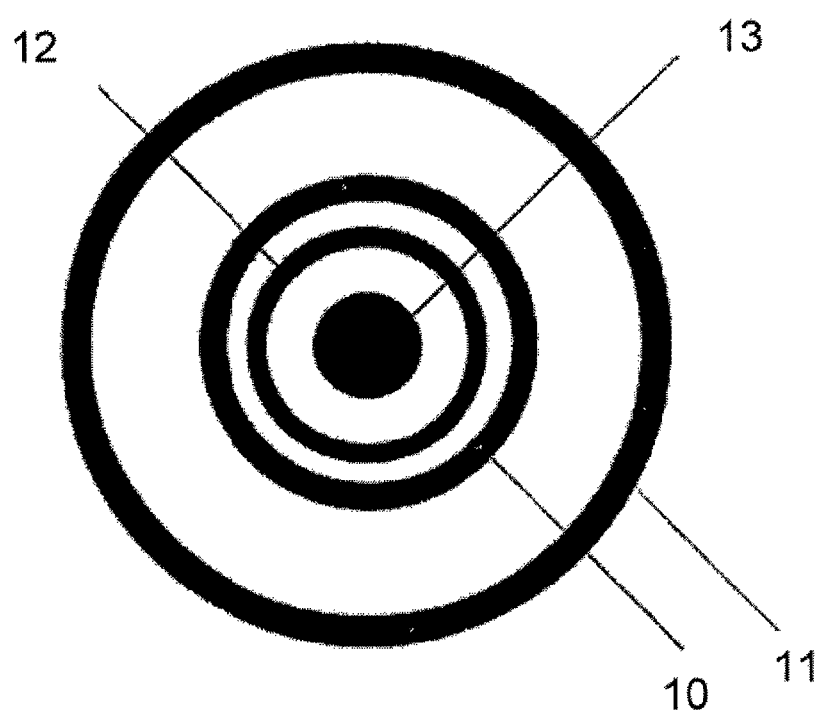
FIG. 1 is a schematic view of the surface of an electrode probe of the present invention.

In order that the invention may be more fully understood, it will now be described, by way of example, with reference to the accompanying drawings in which FIGS. 1 through 10 illustrate embodiments of the present invention.

A preferred method and apparatus of the invention involves contacting a body tissue with one or two pairs of injection electrodes and sensing electrodes, in order to measure impedance with what is referred to as the "two-point impedance analysis and "four point impedance analysis". The body tissue can be either skin (e.g. dermal tissue) or a sub-dermal or subcutaneous tissue (e.g. any body tissue other than the skin). In two point impedance analysis, on pair of injection and sensing electrodes are used, while in four point impedance analysis two pairs of injection and sensing electrodes are used. Such equipment can be referred to as "2 point equipment" or "4 point equipment".

Four point impedance analysis, using implanted electrodes, has been used to examine cardiac function, by detection of alterations in electrical properties of heart muscle tissue (Min, M. et al. "Electrical Impedance and Cardiac Monitoring—Technology, Potential and Applications." *International Journal of Bioelectromagnetism*, v. 5: 53-56, 2003), but until now, it has not been used to measure blood glucose levels in an accurate and reliable manner.

An aspect of the invention utilizes four-point impedance analysis to measure impedance of sub-dermal body tissues (i.e. subcutaneous or below the dermis). The use of four-point impedance analysis of electrical impedance of subcutaneous body tissues provides reproducible impedance measurements which can be accurately correlated to blood glucose levels. By measuring the impedance of sub-dermal tissues, such as muscle, adipose (e.g. fat), blood vessels or blood to determine blood glucose levels, the potential problems associated with the accuracy and reproducibility of prior art methods and apparatuses, including some of the methods and apparatus using skin impedance measurements can be reduced and possibly avoided.

The method and apparatus employing 4-point impedance analysis using two injection electrodes for injecting electrical current into a body tissue, and two sensing electrodes for measuring the voltage or potential of body tissue the body tissue can be skin or a sub-dermal tissue. It would also be understood that an amperometer for measuring the amount of applied current, and a voltmeter for measuring the potential of the body tissue would also be provided. Body tissue as defined herein can be any body tissue. By injecting electrical current with two injection electrodes, the current can be injected at varying depths below the surface of the body tissue to which the injection electrodes have been applied, as described in U.S. Pat. No. 5,353,802 to Ollmar, which is incorporated herein by reference. An aspect of the method and apparatus of the invention comprises injecting electrical current into or below the skin (e.g. sub-dermally or subcutaneously), such that impedance measurements of the underlying or sub-dermal tissue can be obtained. Such measurements of sub-dermal impedance provides an improvement over previous methods since sub-dermal tissues may not be affected by the variables which can affect the reliability of the impedance measurements taken from skin. As such, impedance measurements of sub-dermal tissue can be reproducible, accurate and reliable.

In an aspect of the invention, an impedance spectrometer equipped with a 2-point or a 4-point depth selective electrode probe for non-invasive measurements on human skin is used to obtain impedance measurements of sub-dermal body tissue. For example, the SciBase II™ depth selective spectrometer (SciBase AB, Huddinge, Sweden) can be used. An Impedance Body Segment Analyzer ("IBSA"), modified to include a 4-point electrode probe can also be used (Department of Medical Technology, Huddinge University Hospital, Huddinge, Sweden; Ollmar, Nicander I. (1995) "Information in multi-frequency measurements on intact skin", *Innov. Tech. Biol. Med.* 16: 745-751)). The probe and spectrometer are operatively connected to a computer and/or a microprocessor programmed with appropriate software for presentation and storing of measured impedance data, such as ImpSoft™ (SciBase AB, Huddinge, Sweden). Impedance is measured at several different frequencies in a further aspect of the invention, the method and apparatus uses electrical currents which can between 1 Hz and 10 MHz, and are preferably between 10 Hz and 10 MHz.

A sufficiently high voltage is applied across the injection electrodes to overcome the impedance of the skin, enabling the current to flow at all frequencies. An ideal voltage sensor is used that would not draw current through the voltage sensing electrode. A test current is forced through the injection electrodes and the sensing electrodes detect the ensuing voltage.

In a preferred aspect of the invention, the injection electrodes and the sensing electrodes are in electrically conductive contact with skin tissue, and preferably a skin surface. The 4-point electrode probe surface can consist of four concentric electrodes, which are to be applied to a skin surface of a subject, as shown in FIG. 1. The two outermost electrodes 10, 11 are referred to injection electrodes as they are used for electricity injection into the body tissue. The two inner electrodes 12, 13 are referred to as sensing electrodes as they are used for receiving and sensing the electrical current, which passes through the body tissue. By injecting the electricity with two electrodes, a virtual electrode can be created, which is positioned somewhere in between the two physical injection electrodes. The depth of penetration of the electrical current into the body tissue is dependent on the distance between the two injection electrodes, and the amount of electrical current that is injected through one injection electrode relative to the other. In the SciBase II electrode probe noted above, the system is configured to measure at five predetermined depths between 0.1 and 2 mm below the skin surface, but any number of depths can be programmed. The outermost sensing electrode 12 is also known as a guard electrode as it is used to shield the central sensing electrode 13 from currents passing along the skin surface from the injection electrodes. As these currents have not passed through any body tissue, they do not represent an impedance value which can be correlated to blood glucose level.

In addition to being in contact with the skin, one or more of the injection electrodes or the sensing electrodes can be in electrically conductive contact with a sub-dermal or subcutaneous body tissue, for example, muscle tissue from which impedance is to be measured. All or some of the injection electrodes and the sensing electrodes can also be implanted within the body of the subject, typically they are implanted sub-dermally. For example, the electrodes can be implanted subcutaneously, e.g. on the surface of a large muscle. Alternatively, the injection electrodes can be in conductive contact with skin tissue, preferably a skin surface and the sensing electrodes can be in conductive contact with the body tissue from which impedance is to be measured, such as sub-dermal tissue.

The two injection electrodes can be placed at two different positions on the body of the subject, in order to measure impedance of one or more body segments (e.g. a portion of an arm or a leg) or the whole body. In other words, each pair of injection and sensing electrodes can be located at two different positions. A pair of a first injection electrode and a first sensing electrode are placed in conductive contact with a skin tissue or a sub-dermal body tissue at a first position on the body of the subject, and a second pair of a second injection electrode and a second sensing electrode are placed in conductive contact with a skin tissue or a sub-dermal body tissue at a second position on the body of the subject.

In a further preferred embodiment of the invention, a first injection electrode is placed on a skin surface near the knee of a subject, and a second electrode is placed on a skin surface near the ankle of the same leg of the subject. The sensing electrodes can be placed on the skin surface or inserted below the skin. In this configuration, the impedance of the lower leg, from the knee to the ankle, is measured.

When the injection electrodes and/or the sensing electrodes are in conductive contact with a skin surface, the skin surface can be treated with saline solution prior to contact with the electrode to increase electrical coupling between the skin and the electrode. For example, the skin can be moistened with saline solution for 60 seconds, using a paper tissue soaked with saline solution. Excess saline solution is then wiped off and the electrode(s) placed on the treated site. Also, an electrically conductive gel can improve contact between the skin surface and electrodes to provide more accurate and reproducible measurements. The gel can be left on the skin during the impedance measuring step, i.e. while the electrode is in contact with the skin surface. Such electrically conductive gels would be well known to a person skilled in the relevant art.

In a broad aspect of the invention, determination of the amount of glucose includes comparison of the measured impedance with a predetermined relationship between impedance of body tissue and blood glucose level. For example, blood glucose levels can be determined directly from a blood sample and measuring the blood glucose level with a commercially available glucometer, e.g. an Elite™ Glucometer (Bayer Diagnostics). At the same time, body tissue impedance measurements, using the above-noted configurations of electrodes, can be collected for each directly measured blood glucose level to form a standard set of data for calibrating the apparatus of the invention. The injection electrodes and the sensing electrodes are in operative connection with a computer or a microprocessor programmed to determine the amount of glucose level based upon the measured impedance.

The microprocessor can be programmed to determine the glucose level of a subject based on a principal component analysis and a partial east squares regression analysis of the measured impedance. In principal component analysis ("PCA"), data gathered in an experiment with a large number of variables is accumulated in a data matrix X of size n×k, where the rows n represent the different measurements and the columns k signify the variables, in order to reduce the number of dimensions and therfore find hidden patterns which are not detectable by simple analysis of raw data (Eriksson L. et al. *Multi- and Megavariate Data Analysis*, Umetrics AB).

The principal component analysis algorithm NIPALS splits the data matrix into a new data structure as well as a residual matrix in which the noisy part of the data is gathered. The equation for the PCA decomposition is given by:

$$X = t_1 p_1' + t_2 p_2' + \ldots + t_a p_a' = E$$

$$X = TP' + E \quad (1)$$

where $t_i$ is the i:t principal component score vector, $p_i$ is the i:t principal component loading vector, T is the score matrix and P the loading matrix and E the residual matrix.

Partial least squares regression ("PLS") is the projection of latent structures by means of partial least squares (Eriksson L. et al. (2001) *Multi- and Megavariate Data Analysis*, Umetrics AB). The partial least squares-algorithm NIPALS uses an extra loading weight W, which directly connects to the building relationship of the X and Y. As long as the dominant structures in X agree with the maximum direction of correlation in Y, the loadings P and W remain similar. Should they show significant difference this would imply that the features found in Y do not correlate well to the dominant characteristics in X (Esbensen K. et al. (1994) *Multivariate Analysis in Practise*, Camo A S). The formulas for the decomposition of the two data matrices with the NIPALS algorithm are given below:

$$X = TP' + E \quad (2)$$

$$Y = UQ' + F \quad (3)$$

$$Y = (W(P'W)^{-1}Q')X \quad (4)$$

where T, U are the score matrices and P, W, Q the loading matrices and E, F the residual matrices for X and Y respectively. Y stands for the predicted value from a PLS model. To summarize PLS tries to capture the most variance within each data matrix X and Y and also take into account that the correlation between the two should be as large as possible.

Cross-validation will iteratively calculate a value for the closeness of the fit for the model, called $Q^2$, which is calculated as follows:

$$Q^2 = 1 - \frac{\sum_{i=1}^{n}(y_i - \hat{y}_{ip})^2}{\sum_{i=1}^{n}(y_i - \bar{y})^2} \quad (5)$$

where $y_i$ are the observed response values and $\hat{y}_{ip}$ the predicted response values obtained through cross-validation using only the p:th PLS component and y being the mean of all the measured responses. The closeness of the fit, $Q^2$ for each PLS component revealing its individual significance. If $\hat{y}_{ip}$ is calculated when all significant p PLS components are incorporated, a cumulative score for $Q^2$, called $Q^2_{Cum}$ is attained through the equation above. A $Q^2_{Cum}$ of 0.5 is considered to be good and a value of 0.9 is excellent. However, this value is application specific, depending on what process is modelled. Hence a lower or higher $Q^2_{Cum}$ can be considered good or excellent. The explained variance of Y, $R^2Y_{Cum}$, is then compared with $Q^2_{Cum}$. The results from above-described analysis of the impedance measurements can then presented in an error grid. In the Examples, a BD grid is employed (Parkes J. L., et al. (2000), "A new consensus error grid to evaluate the clinical significance of inaccuracies in the measurement of blood glucose," *Diabetes Care*, 23, pp 1143-1148). Other types of error analysis can be used, such as the Clarke grid (Clarke W. L., et al. (1987) "Evaluating clinical accuracy of systems for self-monitoring of blood glucose", *Diabetes Care*, 10, pp 622-628.; Cox D. J., et al. (1989) "Clarification of Error-Grid Analysis", *Diabetes Care*, 12, pp 235-236). It will be understood that in view of the above discussion and the cited references, persons skilled in the relevant art would understand which multivariate algorithms can be used to correlate impedance measurements with glucose levels, when provided with directly measured glucose levels.

The computer or microprocessor includes an indicator for indication of the determined glucose level. This indicator can include a visual display for the subject to see. The computer of microprocessor can optionally be operatively connected to an insulin pump and means to adjust the amount of insulin flow via the pump to the subject, based on the determined blood glucose level. In the case of implanted electrodes, the electrodes can be operatively attached to a microprocessor, programmed as described above, and the electrodes and the microprocessor placed in a housing, similar to a pacemaker device, which allow for implantation. An insulin pump can also be combined with the implanted electrodes and microprocessor.

Further details of the preferred embodiments of the invention are illustrated in the following Examples which are understood to be non-limiting with respect to the appended claims.

Example 1

Skin impedance was measured using the SciBase II skin impedance spectrometer with 2-point electrode (FIG. 1), applied to a skin surface of a subject. To increase the conductance of the horny layer of the skin, it was moisturized with physiological saline solution. In this experiment the volar forearms of two volunteers were used. One volunteer is diagnosed with Diabetes Mellitus type 1, whilst the other subject is not known to suffer from neither Diabetes nor any other blood or skin related diseases. Impedance was measured every ten minutes for approximately 4 hours during several days.

On the volar forearms of the volunteers, two hairless sites measuring 2×2 cm, located above and below the middle of the arm, were marked. One site at a time was moistened with saline solution during 60 seconds, using a paper tissue with the dimensions 4.5×6.5 cm soaked with 2.5 ml of saline solution. Quickly afterwards excess water was wiped off and the probe was placed on the marked site. The probe rested on the skin with merely its own weight for ten seconds in order to establish a good contact. Skin measurements were then carried out with the impedance spectrometer at five different depth settings using 31 frequencies for each depth. This resulted in 155 magnitude and 155 phase values after a measuring time of 20 seconds.

The data acquired was analysed using PCA to show possible outliers or drifts within the measured data. PLS was then applied to the data in order to correlate the impedance against blood glucose measured in a drop of blood from a fingertip For the non-diabetic subject, the data showed significant fluctuations between consecutive measurements even without changes in blood glucose level. The fluctuations were so severe that the hope of finding any correlation was close to nonexistent. Therefore, the results presented below originate only from the diabetic subject.

Figure 2:
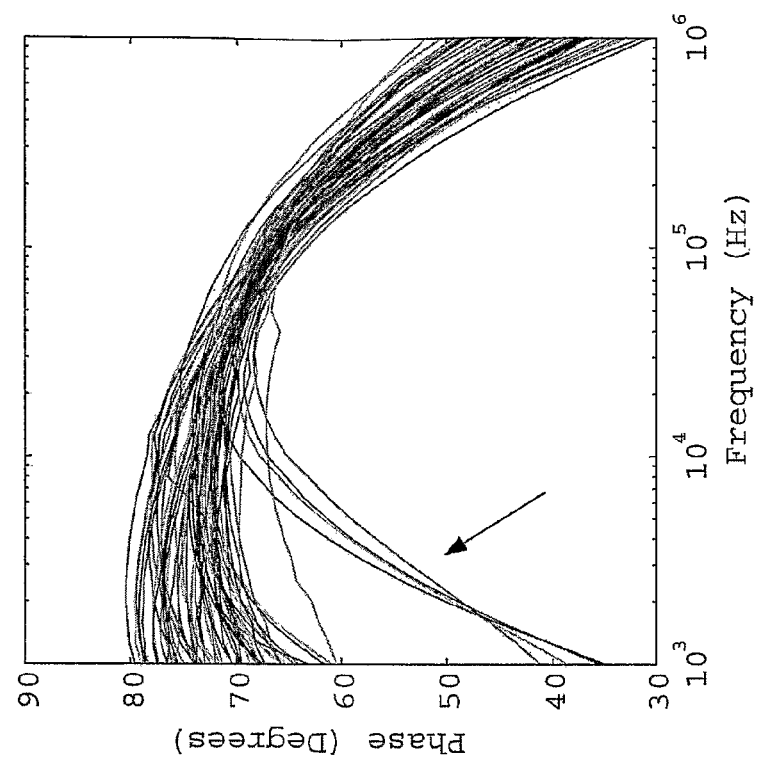
FIG. 2 is data of the first depth setting obtained with an electrode probe of FIG. 1.
Figure 2:
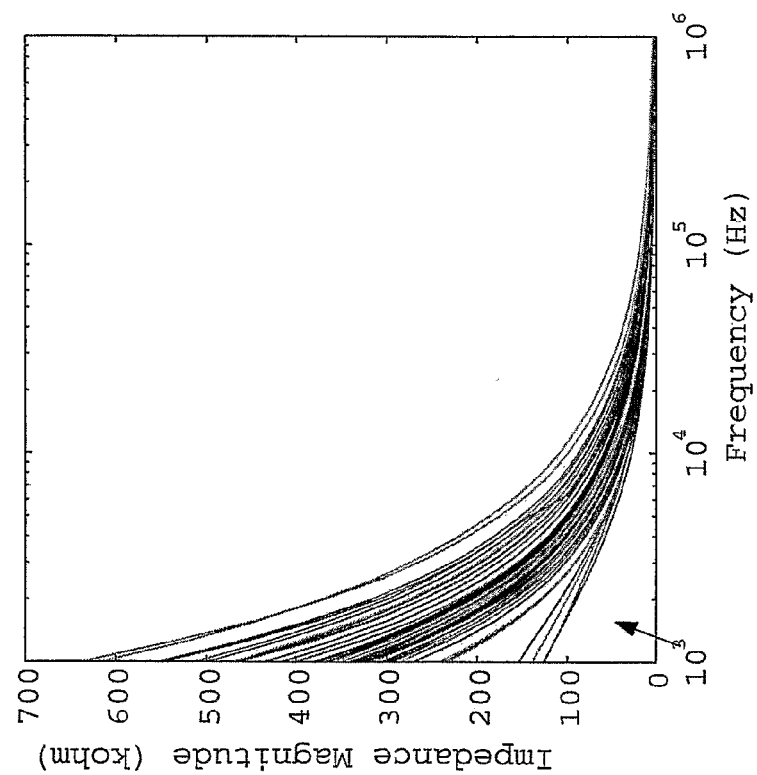
Figure 3:
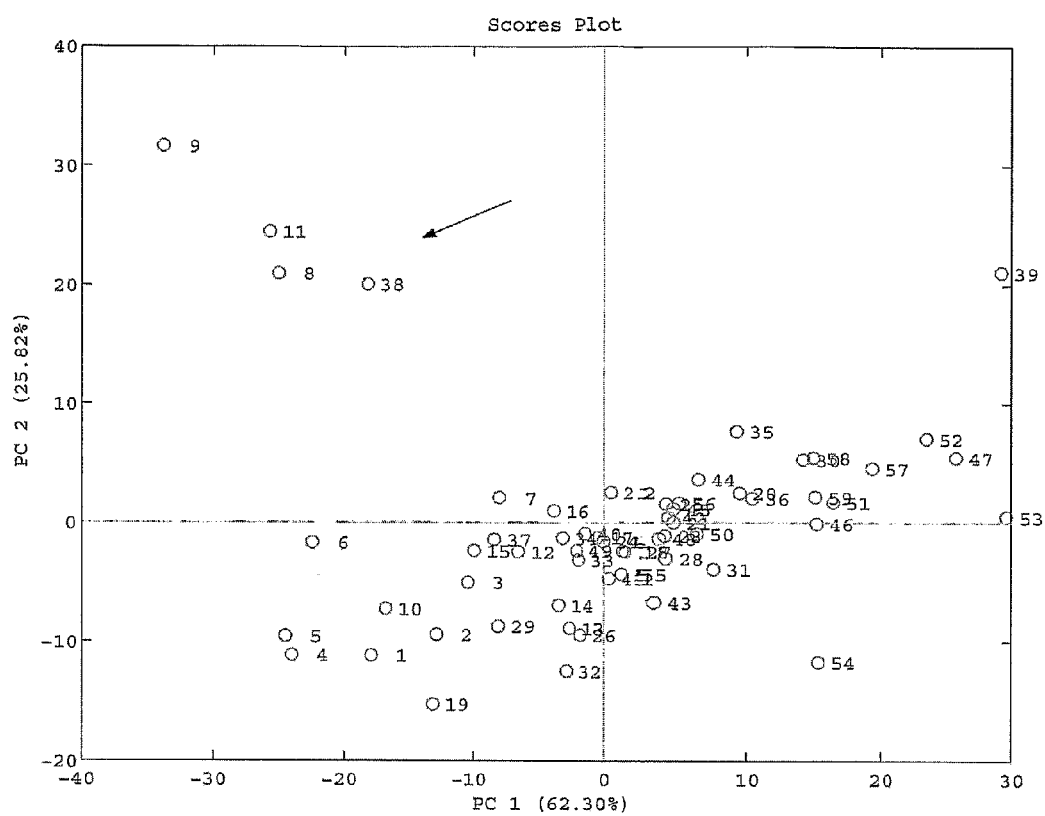
FIG. 3 is the score plot from a PCA model of the data depicted in FIG. 2.

Applying PCA on the raw data quickly showed the existence of four outliers in the score plot (FIG. 3). These outliers correspond to the magnitude and phase curves marked in the raw data plot (FIG. 2). They are probably the result of either too much inundation, excess fluid on the skin surface or long time storage of fluid in the top layers of the skin.

After removing these outliers from the data, PCA was applied once more. No new critical outliers were found and the remaining data are considered to be a good base for further analysis.

Example 2

In the non-invasive experiment of Example 1, a small correlation was detected between glucose concentration and impedance magnitude, suggesting that a correlation could be detected by placement of the electrodes in direct contact with body tissue, in the case muscle tissue.

Body tissue impedance measurements were obtained with a instrument obtained by modifying an Impedance Body Segment Analyzer ("IBSA"), Department of Medical Technology, Huddinge University Hospital, Huddinge, Sweden (Ollmar, Nicander I. (1995) "Information in multi-frequency measurements on intact skin", *Innov. Tech. Biol. Med.* 16: 745-751). The IBSA measures in the frequency range from 5 Hz to 500 kHz and was converted to 4-point impedance measurements for this experiment. Circuitry for separation of current injection and voltage detection was added to the IBSA.

The measurements were performed in the right leg of one volunteer suffering from diabetes mellitus type 1. A Styrofoam form was used to stabilize the leg during the measurement period, since movement will affect the measurements. Two injection electrodes were placed in conductive contact with the skin surface of the subject's leg, and two sensing electrodes, in the form of needles, were inserted below the skin of the subject's leg. The positions of the needles (sensing electrodes) were decided after studies of the human anatomy, as well as discussions with medical personnel. One injection electrode was placed near the knee, and the second injection electrode placed near the ankle. The sensing electrodes were implanted near the middle of the calf muscle, i.e. approximately mid-way between the two injection electrodes.

An estimated blood glucose value for each measurement was obtained using an invasive blood glucose meter (Glucometer Elite XL 3901E, Bayer).

The measurements started approximately 60 minutes after the needles were put into place, in order to ensure a minimum of remaining inflammatory responses (Koschinsky T. Heinemann L. (2001) "Sensors for glucose monitoring: technical and clinical aspects" *Diabetes Metab. Res. Rev.* 17, 113-123).

Impedance values and blood glucose were registered every 10 minutes for roughly four hours. For each impedance measurement, five registrations were made to be able to investigate the deviation within each measurement compared to the deviation between consecutive ones.

To achieve a wide span of blood glucose concentrations in the subject, 75 g of water-free glucose powder dissolved in water were consumed after the first hour. When the blood glucose reached a high enough value, insulin was administered yielding a drop in the glucose value. Lunch was also consumed during the measurement period. At the end of the experiment the blood glucose of the subject was thoroughly checked for a longer time to make sure hypoglycaemia did not set in.

The collected data was analysed in several steps. First the raw data was visualized as is, without any data analysis applied. Thereafter statistical methods box plot, mean value and standard deviation were used to reveal artifacts such as noise. PCA was used to make sure that no outliers would affect the model.

Figure 4:
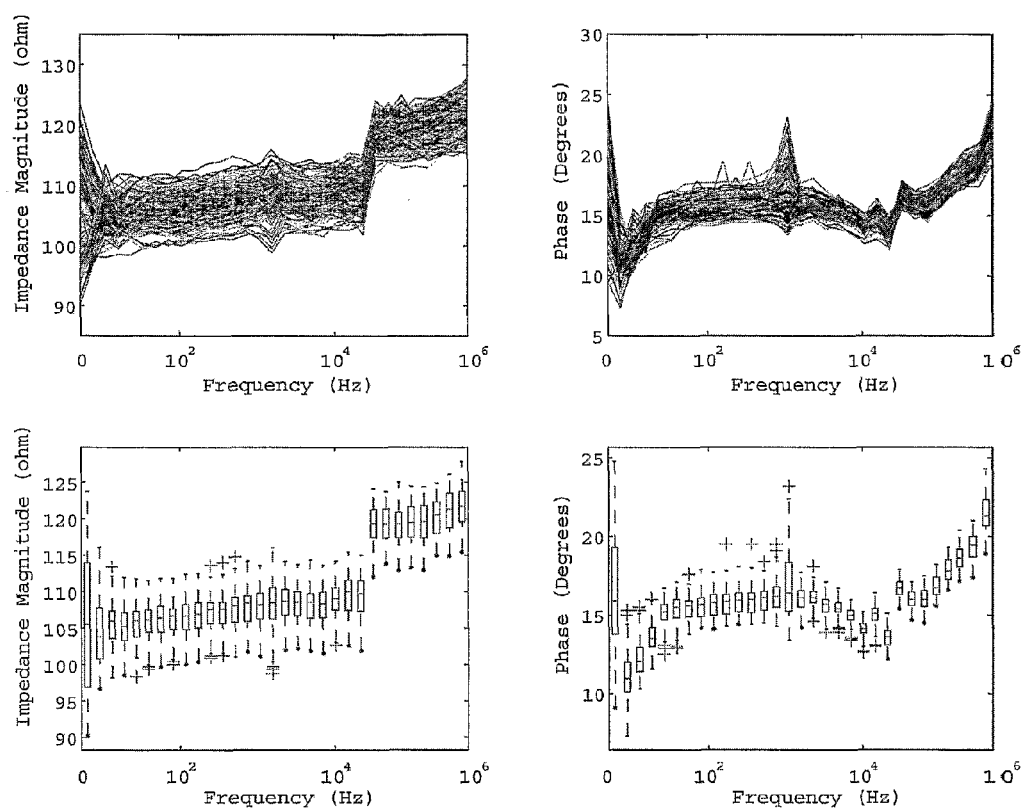
FIG. 4 is a raw data and box plot of raw data of the data obtained using an electrode probe of the present invention.

The raw data gathered from the measurements are shown in FIG. 4. Two injection electrodes in conductive contact with the skin surface of a leg of a subject, and two surface electrodes implanted below the surface of the skin of the leg. The data shows signs of interference at specific frequencies. Since all frequencies are cross-correlated, there should be no apparent discontinuities in the plot. Three distinctive frequency ranges are affected by noise (5-10 Hz, 1-2 kHz and 100-500 kHz) which were dropped from the data analysis.

After those adjustments, the data set was analysed with PCA to assure that all five registrations that were done for each measurement showed similar characteristics area, implies that the total deviation is large within one observation. Although there was background noise, it is evident from the data analysis that there is a correlation between subdermal tissue impedance and the directly measured glucose level.

Example 3

The procedure of Example 2 was repeated, with the subject seated in a Faraday cage constructed in which the walls, floor and ceiling are covered by metal plates made of μ-metal. The computer used for analysis of the measurements was a laptop portable computer, in order to further reduce noise sources. As soon as the needles were put into place, the measurements started. The procedure was the same Example 2 where five registrations were made for each impedance measurement, with one addition. During the measurements, both lunch and 75 g water-free glucose powder was consumed in order to achieve a wide span of blood glucose values Since the raw impedance data contained less noise than before, the mean values of the replicas were considered directly. A PCA model was created based on the mean values of the magnitudes and possible outliers were identified. Thereafter a PLS model was constructed to see if a correlation exists between impedance and blood glucose. Every even sample was used as training data for the model and every other as prediction set. Cross validation of the model was also done using SIMCA.

To validate the model further, the reference glucose vector was permutated a number of times and for each permutation new $Qc2\sim_{,,}s$ and $R^2Y_{,,,,}s$ were calculated using the same amount of PLS components to validate the statistical significance of the model.

Figure 5A:
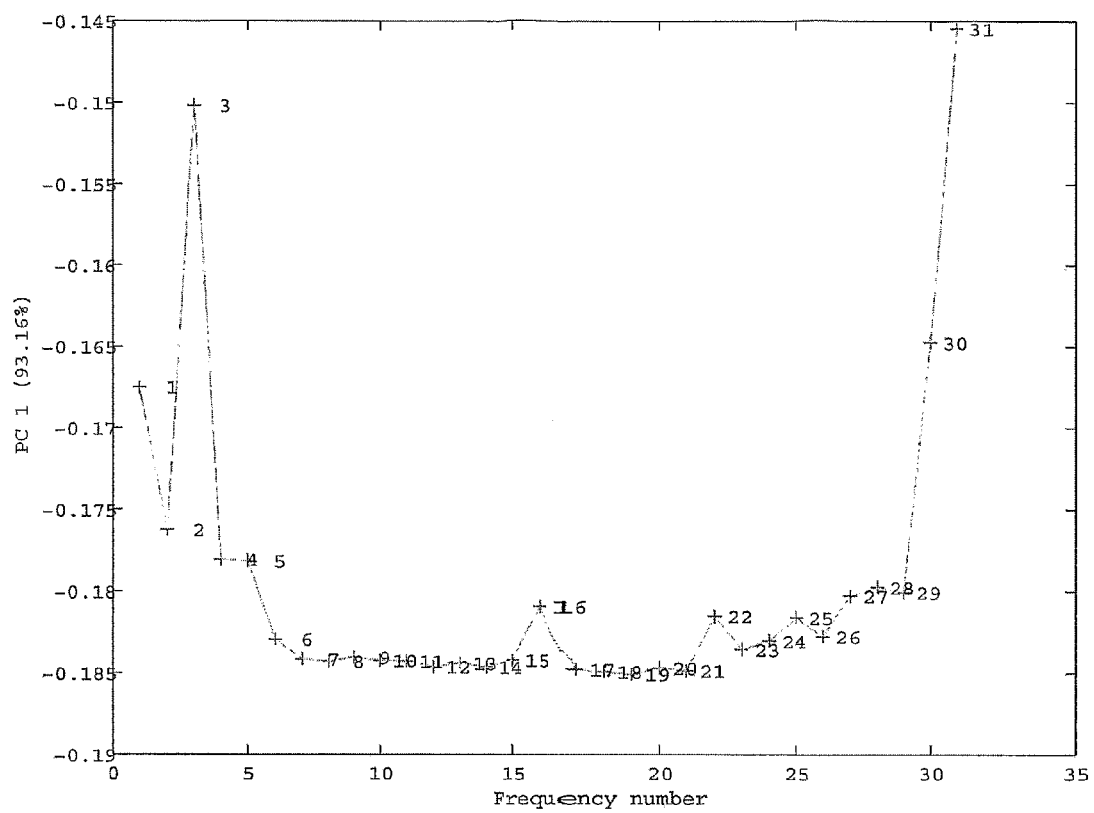
FIG. 5a is a loading plot, from 5 Hz to 500 kHz, for impedance data from and electrode probe of the present invention.
Figure 5B:
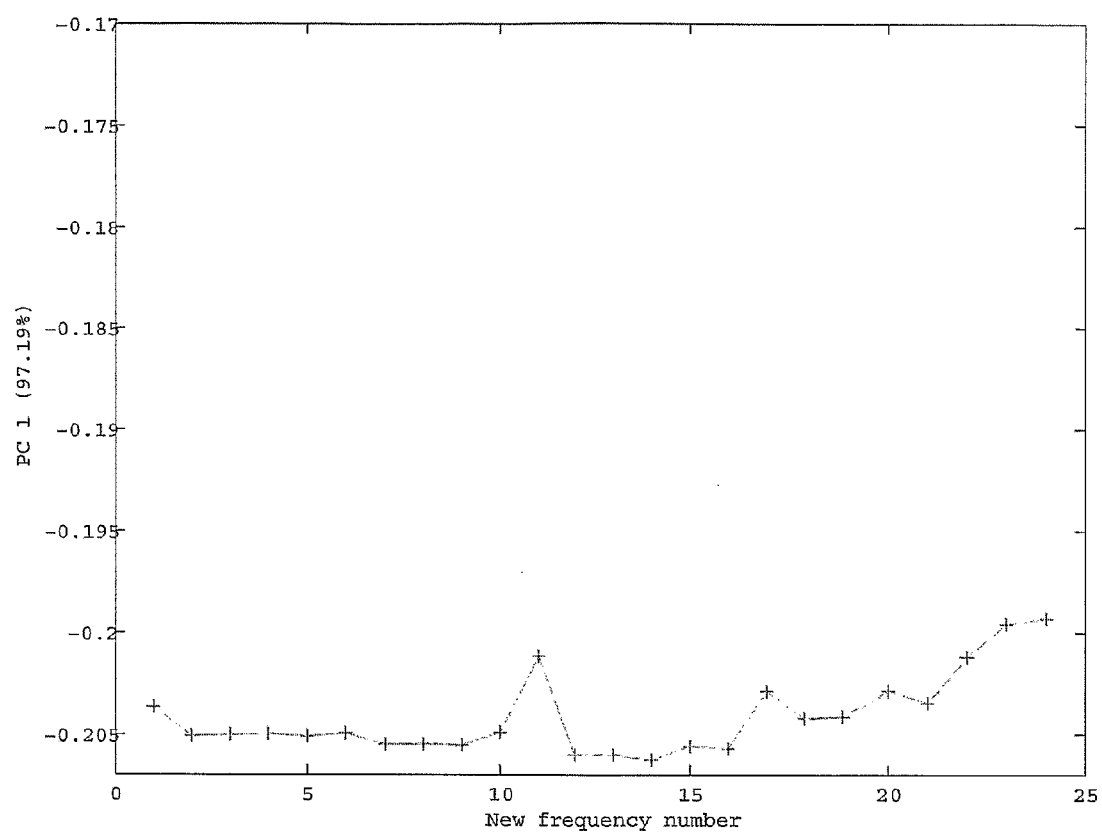
FIG. 5b is a loading plot after excluding problematic frequencies, from 34 Hz to 232 kHz for impedance data from an electrode probe of the present invention.
Figure 6:
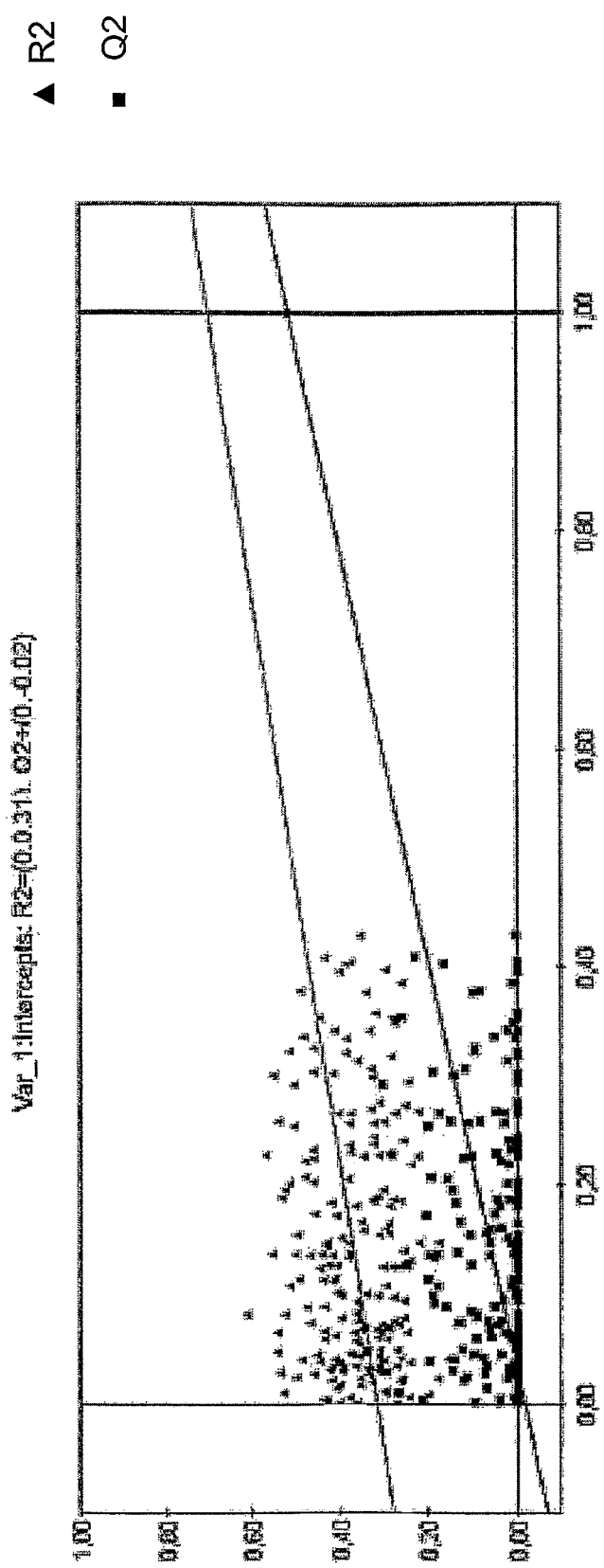
FIG. 6 is a result of the permutation validation of the data of FIG. 5b, wherein the y-axis represents $R^2Y_{cum}$ and $Q^2_{cum}$ and the x-axis shows the correlation between the permuted and original glucose values (Y data). The original $R^2Y_{cum}$ and $Q^2_{cum}$ are the rightmost values. $\Delta = R^2Y_{cum}$ and $\square = Q^2_{cum}$.
Figure 7:
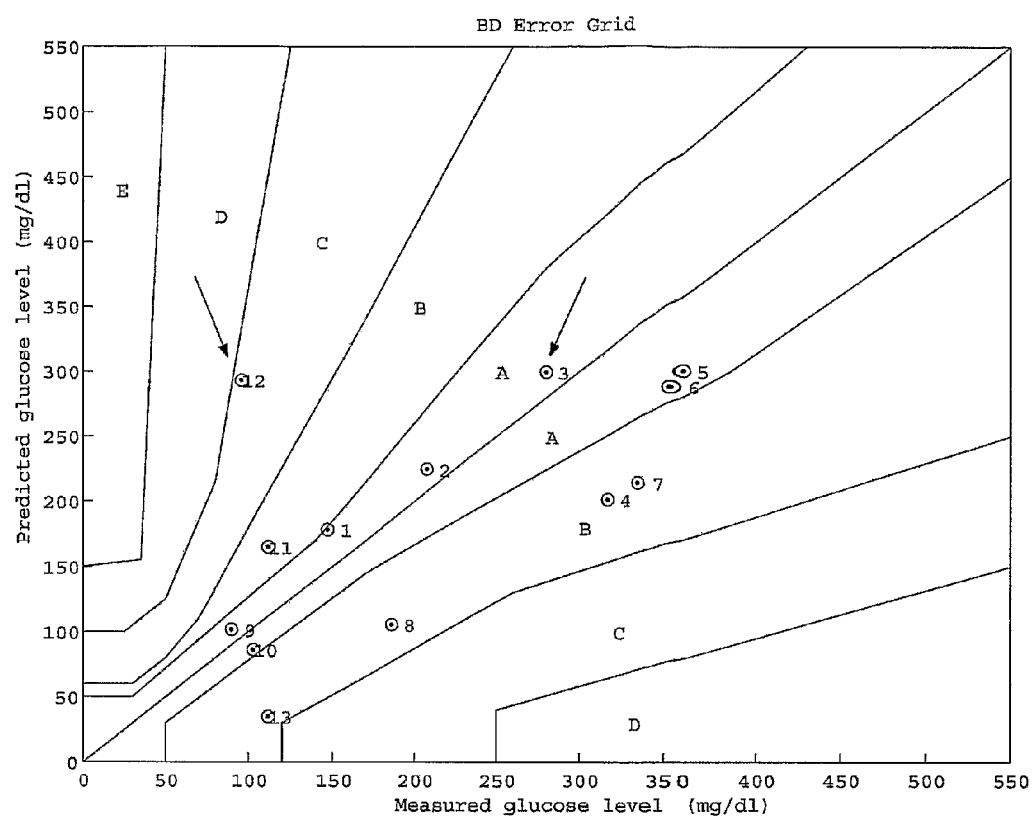
FIG. 7 is a BD error grid, showing the resulting prediction based on the analysis of the data of FIG. 5b and 6, correlating predicted glucose level (based on impedance measurements) to directly measured glucose level.

The first five measurements (i.e. the measurements carried out during the first 50 minutes) were distorted and were discarded. The first five frequencies (i.e. 5-23 Hz) were also excluded, since these were disturbed. It is known that low-frequency measurements are hard to get noise-free. FIG. 5a is a loading plot of the impedance data collected between 5 Hz to 500 kHz. As observed in the loading plots (FIGS. 5a,b), the two highest frequencies (340 and 500 kHz) are separated from the rest, indicating that these frequencies were affected by noise as well and hence they were excluded. FIG. 5b is a loading plot after excluding problematic frequencies, from 34 Hz to 232 kHz for impedance data from an electrode probe of the present invention FIG. 7 shows the result of the 200 permutations of the Y data. For each permutation new values for $R^2Y_{cum}$, and $Q^2_{cum}$ have been calculated. The fact that all the new $R^2Y_{cum}$ and $Q^2_{cum}$ values remain beneath the values calculated for the model indicates its statistical significance. The correlation between blood glucose level and impedance found in this experiment is quite clear. The $Q^2_{cum}$ is 0.516 indicating that the model must be considered to be significant from a statistical point-of-view. The validation through permutation of the Y data enforced the significance of the model. As can be seen the BD error grid (FIG. 7), 7 values are categorized as A and 5 values are categorized as B (see Parkes J. L., et al. (2000), "A new consensus error grid to evaluate the clinical significance of inaccuracies in the measurement of blood glucose," *Diabetes Care*, 23, pp 1143-1148). From a clinical point-of-view, the model based on every other sample is significant and the method provides a correlation between measured impedance and blood glucose level.

Example 4

The SciBase II was used in place of the modified IBSA of Examples 2 and 3, since it is much less sensitive to background noise. The experiment was carried out in an unshielded environment. Attempts were made to reduce possible noise sources, such as turning off nearby computer screens. The same experimental procedure as Examples 2 and 3 was used.

The SciBase II is a two-point impedance measurement device. As such, the two needles were placed subcutaneously in the upper and lower part of the left arm of the same volunteer as in previous experiments. To assure that the needles would not cause more than an initial inflammatory response, the sharp point of the needles were pushed through, so that they exited the skin a few centimeters from the insertion site. Blood samples were taken from the finger tips of the right hand and were used for direct measurements of blood glucose concentration.

The measurements did not start until two hours after the incision of the needles. Both glucose level and impedance values were registered simultaneously every five minutes during the entire experiment, that lasted almost four hours. For each impedance measurement, two registrations were done to compare the deviation within each measurement with the deviation between consecutive ones.

Lunch was consumed in the beginning of the measurements, and half way through 75 g of water-free glucose powder dissolved in a glass of water was consumed to achieve a wide span of blood glucose concentrations in the subject. Insulin was administered when the blood glucose level reached approximately 300 mg/dl. At the end of the experiment, the subject was observed during a longer time period, to assure that the subject returned to and remained in euglycaemia.

The two replicas from the impedance measurements were examined both in a raw data plot and in a PCA score plot. Possible outliers were also identified in the score plot. After this, a PLS model was constructed and $R^2Y$ and $Q^2$ were calculated using the same cross validation method as before. Permutations of the Y data were also performed to validate the model further. In the end a PLS model was constructed from every other sample and the rest were used as a prediction set.

Figure 8:
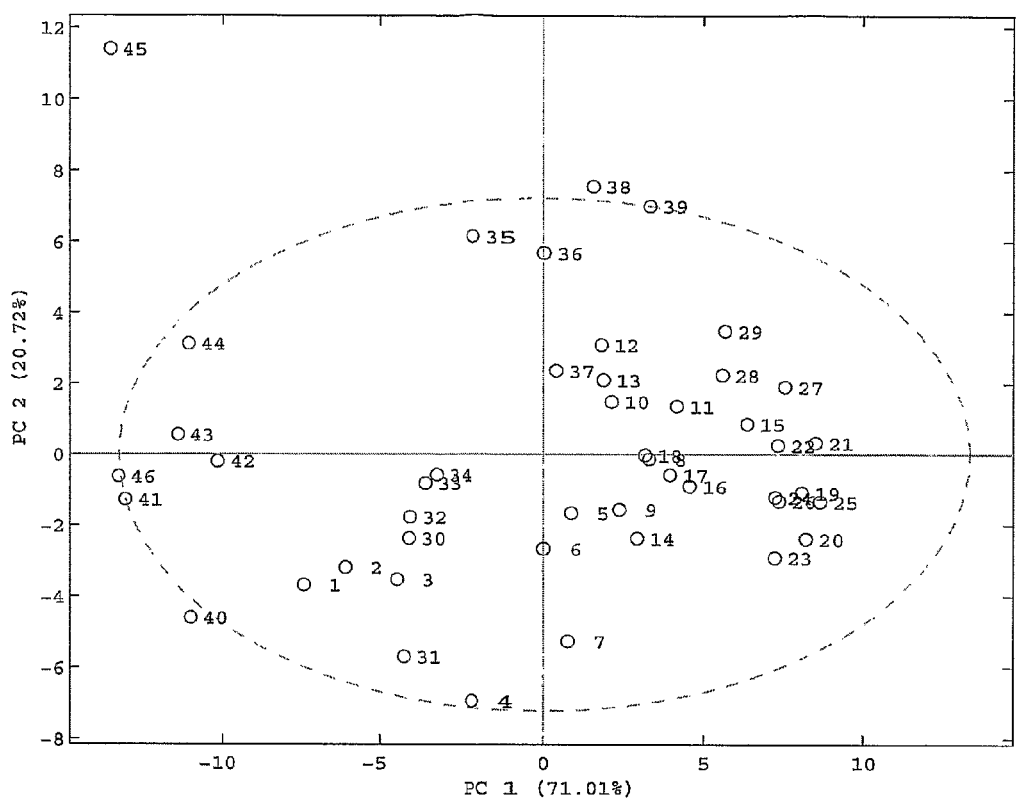
FIG. 8 is a PCA score plot of the two first principle components.
Figure 9:
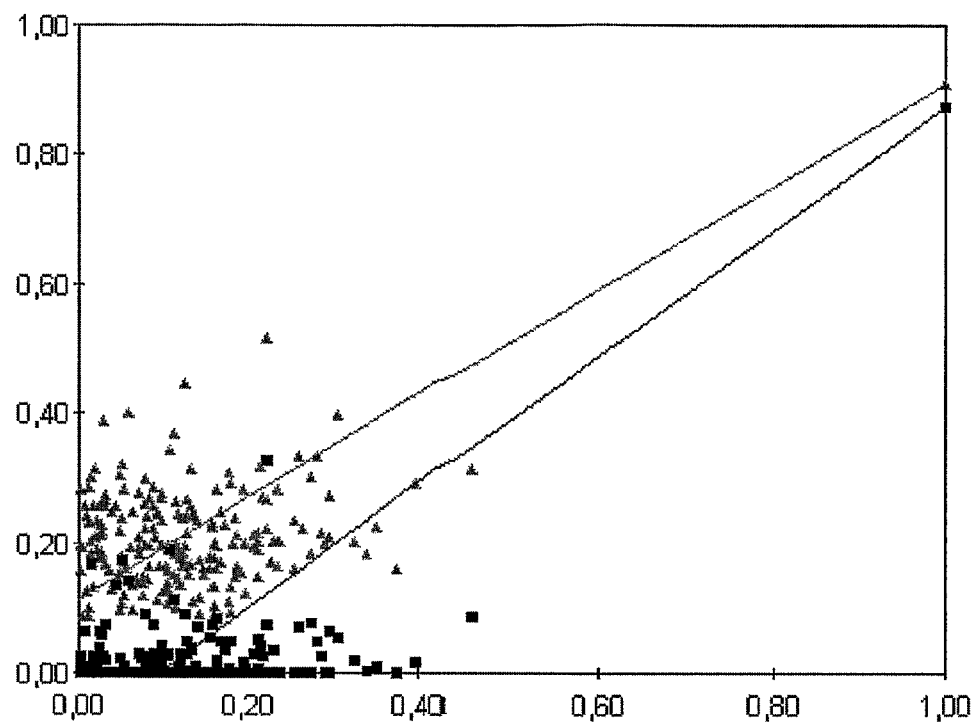
FIG. 9 is the results of the permutation validation, wherein the y-axis represents $R^2Y_{cum}$ and $Q^2_{cum}$ and the x-axis shows the correlation between the permuted and original glucose values (Y data). The original $R^2Y_{cum}$ and $Q^2_{cum}$ are the rightmost values. $\Delta = R^2Y_{cum}$ and $\square = Q^2_{cum}$
Figure 10:
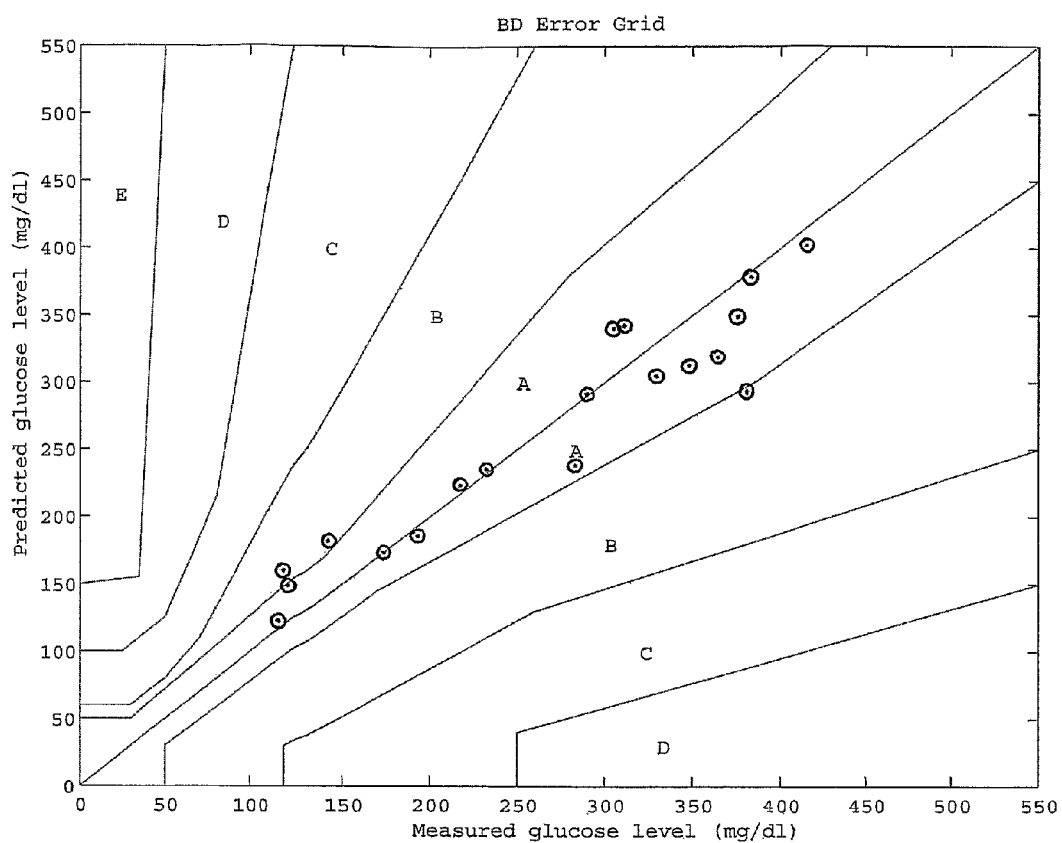
FIG. 10 is the resulting prediction based on every other sample, presented in a BD error grid to show clinical significance.

No measurements were discarded due to initial inflammatory response in this experiment, since the measurements did not start until two hours after the insertion of the needles. A PCA score plot was constructed anyhow to reveal possible outliers later during the experiment (FIG. 8). The seven last measurements (sample 40-46) were found to be outliers and were discarded. No frequencies were found to deviate substantially from the rest and thus all frequencies were included in the model. Thereafter a PLS model was created on the first 39 measurements. Cross validation was performed to obtain values for $R^2Y_{cum}$ and $Q^2_{cum}$. The conclusion was made that four components should be used, since increasing from four to five PLS components only gave a minor change in Y variance and $Q^2$. For further validation, the Y data was permuted 200 times using the same randomizing seed as before. New values for $R^2Y_{cum}$ and $Q^2_{cum}$ were calculated for each permutation. As seen in FIG. 9, all the new values remained well below the original $R^2Y_{cum}$ and $Q^2_{cum}$ which is another indication of an accurate model.

Another validation was performed as before, where half the data were used as a training set and the other half as a prediction set. The result from this prediction is shown in a BD error grid in FIG. 10. Using every second point for building the model and the rest for prediction gave a very significant model from both a clinical and statistical point-of-view. In the BD error grid (FIG. 10) only 3 points were categorized outside A and all these were categorized in B.

The $Q^2_{cum}$ calculated for the model by using cross validation was 0.875 and $R^2Y_{cum}$ 0.909 for four PLS components. This is a close to excellent model when only considering these values and thus the correlation between blood glucose concentration and sub-dermal or sub-cutaneous impedance is even stronger.

Numerous modifications, variations and adaptations may be made to particular embodiments of the invention described The embodiments of the invention in which an exclusive property or privilege is claimed are defined as follows:

1. An apparatus implantable in the sub-dermal tissue body tissue of a subject for measuring or monitoring blood glucose level in the subject, the apparatus being adapted to measure impedance of the body tissue of the subject resulting from an electrical current flowing through said body tissue and to determine a blood glucose level of said subject based on the measured impedance, wherein the body tissue is sub-dermal or subcutaneous tissue of said subject, and wherein the apparatus is a four-point apparatus that comprises:

one pair of injection electrodes adapted for injection of the electrical current into the body tissue, wherein the electrical current is passed from one of the injection electrodes to the other of the injection electrodes through the body;

one pair of sensing electrodes adapted to detect the resulting voltage caused by the current flowing between the pair of injection electrodes and through said body tissue;

a device for measuring impedance of the body tissue, said device being operatively connected to the pair of sensing electrodes and adapted to receive the voltage detected by the sensing electrodes, wherein the impedance of the body tissue is measured based on the voltage detected by the pair of sensing electrodes;

a microprocessor operatively connected to the device for measuring impedance and being programmed to determine the blood glucose level in the subject by correlating the measured impedance with a predetermined relationship between impedance and glucose levels, and wherein the injection electrodes, the sensing electrodes, the device for measuring impedance and the microprocessor are contained in a housing allowing for implantation sub-dermally;

and wherein the electrical current is an alternating, AC, current having a frequency of less than 10 MHz.

2. The apparatus of claim 1 wherein the sub-dermal body tissue is muscle, fat or blood vessels.

3. The apparatus of claim 1 further comprising an amperometer, a voltmeter and source of electric current for measuring the impedance of the body tissue between said injection electrodes and said sensing electrodes; wherein the amperometer and source of electric current are in operative connection with the injection electrodes and the voltmeter is in operative connection with the sensing electrodes.

4. The apparatus of claim 3 wherein said electrical current is provided at a plurality of frequencies in a range of 1 Hz to 10 MHz.

5. The apparatus of claim 1 wherein the microprocessor is operatively connected to an insulin pump and includes means to adjust the amount of insulin flow via the pump to the subject based on the calculated blood glucose level.

6. The apparatus of claim 1 further comprising means for calibrating the apparatus against a directly measured glucose level of said subject.

7. The apparatus of claim 1 wherein the microprocessor is programmed to determine the glucose level of a subject based on a principal component analysis and a partial least squares regression analysis.

8. The apparatus of claim 1 further comprising an indicator operatively connected to the microprocessor for indication of the calculated blood glucose level.

9. The apparatus of claim 8 wherein the indicator comprises a visual display.

10. The apparatus of claim 1 wherein the apparatus is adapted to be implanted in the body tissue for which the impedance is to be measured.

11. The apparatus of claim 1 wherein said electrodes are adapted to measure impedance at one or more depths ranging from 0.1 mm to 2 mm.

12. The apparatus of claim 1, wherein the device for measuring impedance is a voltmeter.

13. The apparatus of claim 1, wherein the injection and sensing electrodes are circular electrodes.

* * * * *